United States Patent
Kondoh

(10) Patent No.: US 9,428,057 B2
(45) Date of Patent: Aug. 30, 2016

(54) INFORMATION PROVISION DEVICE FOR USE IN VEHICLE

(71) Applicant: NISSAN MOTOR CO., LTD., Yokohama-shi, Kanagawa (JP)

(72) Inventor: Takayuki Kondoh, Kanagawa (JP)

(73) Assignee: NISSAN MOTOR CO., LTD., Yokohama-Shi (JP)

( * ) Notice: Subject to any disclaimer, the term of this patent is extended or adjusted under 35 U.S.C. 154(b) by 0 days.

(21) Appl. No.: 14/971,498

(22) Filed: Dec. 16, 2015

(65) Prior Publication Data

US 2016/0101696 A1    Apr. 14, 2016

Related U.S. Application Data

(62) Division of application No. 14/112,456, filed as application No. PCT/JP2012/002091 on Mar. 26, 2012, now Pat. No. 9,256,989.

(30) Foreign Application Priority Data

Apr. 20, 2011    (JP) .................. 2011-094343

(51) Int. Cl.
| | |
|---|---|
| *G06F 15/18* | (2006.01) |
| *B60K 35/00* | (2006.01) |
| *B60W 40/09* | (2012.01) |
| *B60W 50/14* | (2012.01) |
| *A61B 5/18* | (2006.01) |

(Continued)

(52) U.S. Cl.
CPC ............... *B60K 35/00* (2013.01); *A61B 5/18* (2013.01); *B60W 40/09* (2013.01); *B60W 50/14* (2013.01); *G07C 5/00* (2013.01); *G08G 1/166* (2013.01); *G08G 1/16* (2013.01)

(58) Field of Classification Search
None
See application file for complete search history.

(56) References Cited

U.S. PATENT DOCUMENTS 5,285,523 A * 2/1994 Takahashi ........... F16H 61/0213
701/1
6,061,610 A * 5/2000 Boer ...................... B60K 28/06
180/272

(Continued)

FOREIGN PATENT DOCUMENTS

| JP | 2005-157662 A | 6/2005 |
|---|---|---|
| JP | 2006-174960 A | 7/2006 |

(Continued)

*Primary Examiner* — Rami Khatib
*Assistant Examiner* — Navid Ziaeianmehdizadeh
(74) *Attorney, Agent, or Firm* — Foley & Lardner LLP

(57) ABSTRACT

A first driving instability determining unit estimates driving instability based on a difference value between plural traveling state distributions of different time ranges on the basis of the traveling state data. A second driving instability determining unit estimates driving instability by a process different from the process used in the first driving instability determining unit. A learning completion determining unit determines that the learning is completed when a predetermined learning time elapses from the start of collection of the traveling state data, depending on a degree of learning at which the traveling state distribution calculated by a first traveling state distribution calculating unit is matched with the driving characteristic of a driver. An instability selecting unit selects the instability estimated by the first driving instability determining unit when the learning is completed and selects the instability estimated by the second driving instability determining unit when the learning is not completed.

11 Claims, 13 Drawing Sheets

(51) Int. Cl.
*G07C 5/00* (2006.01)
*G08G 1/16* (2006.01)

(56) References Cited

U.S. PATENT DOCUMENTS

| | | | | |
|---|---|---|---|---|
| 7,996,130 B2* | 8/2011 | Zhang | ................ | B60T 8/17551 |
| | | | | 340/439 |
| 8,315,757 B2 | 11/2012 | Yamamura et al. | | |
| 8,742,936 B2* | 6/2014 | Galley | ................ | B60K 28/066 |
| | | | | 340/439 |
| 2007/0080816 A1* | 4/2007 | Haque | ................ | B60K 28/066 |
| | | | | 340/576 |
| 2008/0186154 A1* | 8/2008 | Haug | ................ | B62D 15/029 |
| | | | | 340/435 |
| 2009/0234552 A1* | 9/2009 | Takeda | ................ | B60W 30/16 |
| | | | | 701/96 |
| 2010/0198456 A1* | 8/2010 | Komori | ................ | B60W 40/09 |
| | | | | 701/33.4 |
| 2010/0318254 A1* | 12/2010 | Yamamura | ............ | B60W 40/12 |
| | | | | 701/31.4 |
| 2011/0153532 A1* | 6/2011 | Kuge | .................... | B60W 40/09 |
| | | | | 706/12 |
| 2012/0041641 A1* | 2/2012 | Kuge | .................... | B60K 35/00 |
| | | | | 701/36 |
| 2013/0325202 A1* | 12/2013 | Howard | ................ | B60W 30/08 |
| | | | | 701/1 |

FOREIGN PATENT DOCUMENTS

| | | |
|---|---|---|
| JP | 2007-026271 A | 2/2007 |
| JP | 2009-009495 A | 1/2009 |
| JP | 2010-072800 A | 4/2010 |
| JP | 2010-198120 A | 9/2010 |
| WO | WO-2009/013815 A1 | 1/2009 |

\* cited by examiner

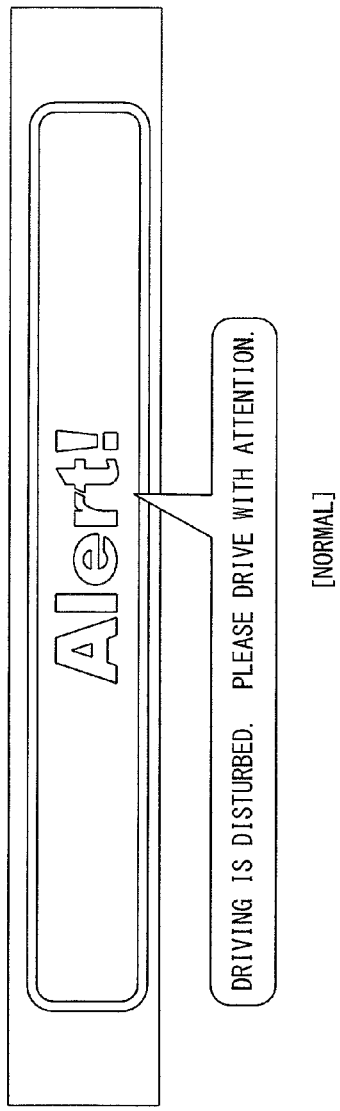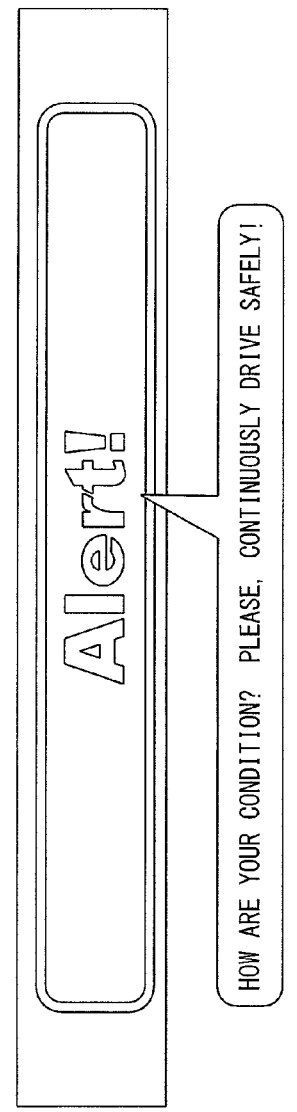

| SIGN | NAME |
|---|---|
| $\tilde{\theta}n$ | θn-tilde SMOOTHED STEERING ANGLE VALUE |
| $\hat{\theta}n$ | θn-hat ESTIMATED STEERING ANGLE VALUE |

| SECTION bi | RANGE OF STEERING ANGLE PREDICTION ERROR θ | PROBABILITY pi |
|---|---|---|
| b1 | $-\infty \sim -5\alpha$ | p1 |
| b2 | $-5\alpha \sim -2.5\alpha$ | p2 |
| b3 | $-2.5\alpha \sim -\alpha$ | p3 |
| b4 | $-\alpha \sim -0.5\alpha$ | p4 |
| b5 | $-0.5\alpha \sim 0.5\alpha$ | p5 |
| b6 | $0.5\alpha \sim \alpha$ | p6 |
| b7 | $\alpha \sim 2.5\alpha$ | p7 |
| b8 | $2.5\alpha \sim 5\alpha$ | p8 |
| b9 | $5\alpha \sim \infty$ | p9 | ured, i.e., when the normal driving characteristics are not
INFORMATION PROVISION DEVICE FOR USE IN VEHICLE

CROSS-REFERENCE TO RELATED APPLICATIONS

This application is a divisional application of U.S. application Ser. No. 14/112,456, filed Oct. 17, 2013, which is the National Stage Application of International Application No. PCT/JP2012/002091, filed Mar. 26, 2012, which claims priority to Japanese Application No. 2011-094343, filed Apr. 20, 2011, the entire contents of all are incorporated herein by reference.

TECHNICAL FIELD

The present invention relates to a technique of presenting an unstable driving state to a driver.

BACKGROUND ART

In a driving support apparatus for a vehicle described in Patent Document 1, a long-time traveling state distribution corresponding to normal driving characteristics and a short-time traveling state distribution corresponding to current driving characteristics are calculated and an unstable driving state is determined on the basis of the magnitude of a difference between the calculated two distributions. It is stated that it is possible to accurately detect an unstable state regardless of a variation in traffic environment according to this method.

PRIOR ART DOCUMENT

Patent Document

Patent Document 1: JP 2009-9495 A

SUMMARY OF THE INVENTION

Problem to be Solved

However, in the technique disclosed in Patent Document 1, when learning for acquiring a long-time traveling state distribution is not completed to such an extent that the normal driving characteristics are regarded as being understood, i.e., when the normal driving characteristics are not understood, the detection accuracy of a driver's unstable driving state is lowered.

The present invention is made in view of the above-mentioned circumstances and an object thereof is to present an unstable driving state to a driver even when learning of normal driving characteristics is not completed.

Solution to the Problem

In order to achieve the above-mentioned object, according to an aspect of the present invention, there is provided a first driving instability determining unit for estimating driving instability based on a difference between plural traveling state distributions of different time ranges on the basis of acquired traveling state data. According to an aspect of the present invention, there is provided a second driving instability determining unit for estimating the driving instability on the basis of the traveling state data through the use of a process different from the estimation process of the first driving instability determining unit. According to an aspect of the present invention, the instability estimated by the first driving instability determining unit is selected when a predetermined learning time elapses from the start of collection of the traveling state data and it is determined that the learning is completed, and the instability estimated by the second driving instability determining unit when it is determined that the learning is not completed. According to an aspect of the present invention, instability information based on the selected instability is presented to a driver.

Advantageous Effects of the Invention

According to an aspect of the present invention, it is possible to present an unstable driving state to a driver depending on the driving instability estimated by the second driving instability determining unit even when the learning for acquiring the traveling state distributions used by the first driving instability determining unit is not completed to such an extent that the normal driving characteristics are regarded as being understood.

BRIEF DESCRIPTION OF THE DRAWINGS

FIGS. 4A and 4B are diagrams+ illustrating an example of information presented to a driver;

DESCRIPTION OF EMBODIMENTS

First Embodiment

First, a first embodiment of the present invention will be described with reference to the accompanying drawings.
(Configuration)

Figure 1:
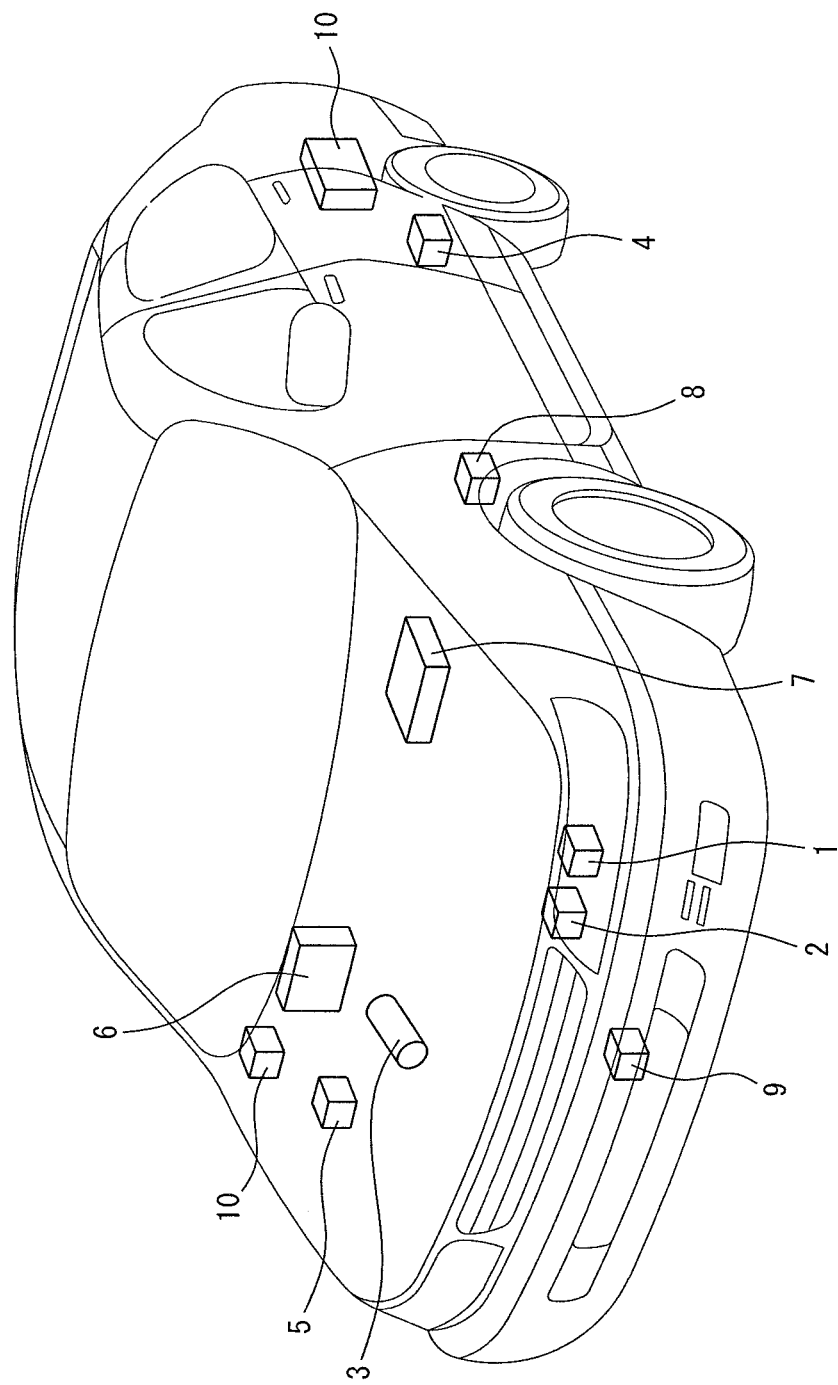
FIG. 1 is a diagram illustrating a configuration of a vehicle according to embodiments of the present invention.

FIG. 1 is a diagram illustrating a configuration of a vehicle having an information provision device for use in vehicle according to this embodiment mounted thereon.

As shown in FIG. 1, a vehicle of this embodiment includes an accelerator pedal opening degree sensor 1, a brake pedal operation amount sensor 2, a steering angle sensor 3, a vehicle velocity sensor 4, a blinker detecting sensor 5, a meter display 6, a navigation system 7, a G sensor 8, a vehicle ahead detecting device 9, and a controller 100. The vehicle to which the present invention is applied does not have to include the above-mentioned sensors and other overall equipment. The sensors used in other embodiments are described together.

The accelerator pedal opening degree sensor 1 detects an opening degree (instructed acceleration value) of an accelerator pedal as an instructed acceleration value. The detected opening degree is output to the controller 100.

The brake pedal operation amount sensor 2 detects an operation amount (instructed braking value) of a brake pedal as an instructed braking value. The detected operation amount is output to the controller 100.

The steering angle sensor 3 is, for example, an angle sensor attached to the vicinity of a steering column or a steering wheel (not shown) and detects a steering angle subjected to a driver's steering operation based on rotation of a steering shaft. The detected steering angle is output to the controller 100.

The vehicle velocity sensor 4 detects a vehicle velocity, for example, by detecting the number of revolutions of a vehicle wheel. The detected vehicle velocity is output to the controller 100. The vehicle velocity sensor 4 may detect the vehicle velocity on the basis of a signal to the meter display 6.

The blinker detecting sensor 5 detects a blinker state of a blinker lever. The detected blinker state is output to the controller 100.

The information presentation device outputs an alarm or other presentations as a sound or an image in response to a control signal from the controller 100. The information presentation device includes a speaker 10 that provides information to a driver, for example, using a buzzer sound or a voice, and a display unit that provides information through a display of an image or texts. A display monitor of the navigation system 7 may be used in common as the display unit.

The navigation system 7 includes a GPS receiver, a map database, and a display monitor and is a system that performs route search, route guidance, and the like. The navigation system 7 is capable of acquiring information on such as a type of a road on which the vehicle travels or a width of the road on the basis of the current position of the vehicle acquired from the GPS receiver and road information stored in the map database.

The G sensor 8 detects a longitudinal acceleration or a transverse acceleration generated in the vehicle. The detected acceleration is output to the controller 100.

The vehicle ahead detecting device 9 detects other vehicles and other objects present on the front side in the traveling direction of the vehicle. In this embodiment, the distance to an object is detected. The vehicle ahead detecting device 9 includes, for example, a laser distance meter. The detected distance is output to the controller 100 as information for calculating an inter-vehicle distance, an inter-vehicle time, a relative velocity, and the like.

The controller 100 is an electronic control unit including a CPU and CPU peripheral components such as a ROM and a RAM, and includes an information providing unit 100A that performs an information provision control process. The information providing unit 100A of the controller 100 analyzes driving characteristics of a driver on the basis of the signals detected by the accelerator pedal opening degree sensor 1, the brake pedal operation amount sensor 2, the steering angle sensor 3, and the like and determines a degree of driving instability such as a disorder of a driver's driving operation. The information providing unit 100A presents an alarm or other information to the driver depending on the degree of driving instability to attract the driver's attention.

Figure 2:
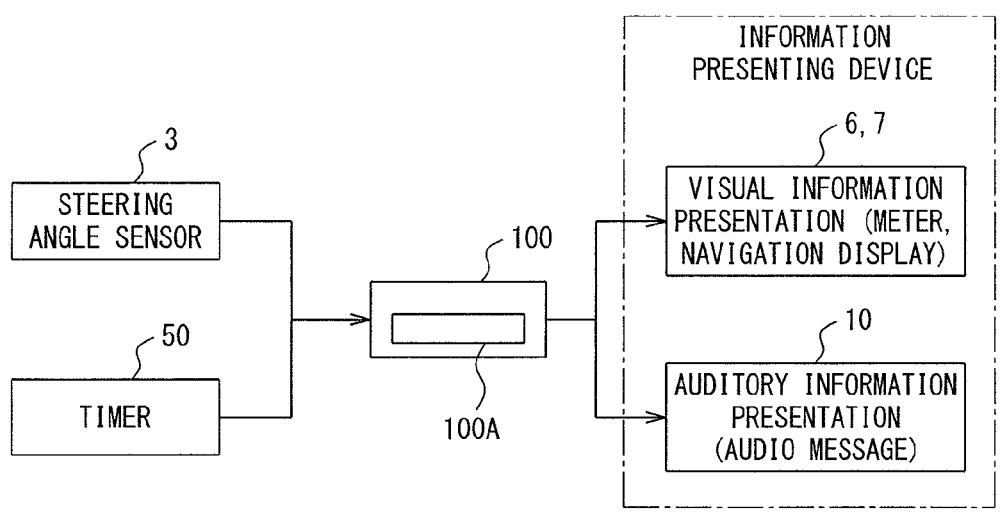
FIG. 2 is a diagram illustrating an example of a system configuration according to a first embodiment to a fourth embodiment of the present invention.

FIG. 2 is a diagram illustrating an example of a system configuration of an information provision device for use in a vehicle including the information providing unit 100A according to this embodiment.

The information provision device for use in a vehicle according to this embodiment uses information from the steering angle sensor 3 as traveling state data, as shown in FIG. 2. A visual information presenting device and an auditory information presenting device are exemplified as an information presenting device. The visual information presenting device is, for example, the meter display 6 or the display unit of the navigation system 7. The auditory information presenting device is, for example, the speaker 10.

The timer 50 is used to acquire a traveling time from the start of collection of the traveling state data.

The same configuration as in the system configuration shown in FIG. 2 is employed by systems according to a second embodiment to a fourth embodiment to be described later.

Figure 3:
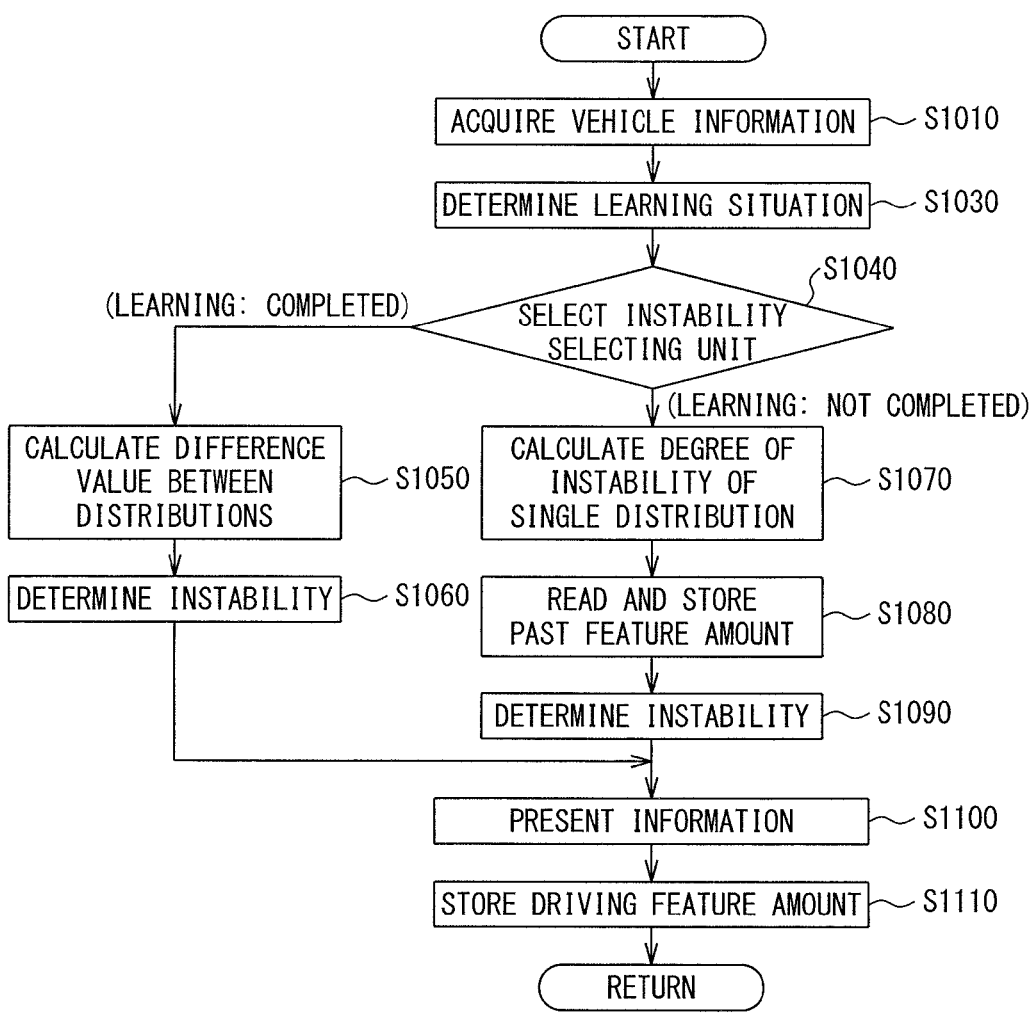
FIG. 3 is a diagram illustrating a process in an information providing unit according to the first embodiment of the present invention.

The process of the information providing unit 100A will be described with reference to FIG. 3. The process of the information providing unit 100A is performed in a predetermined control cycle (for example, 100 msec).

First, in step S1010, the information providing unit 100A acquires the following data as vehicle information data. That is, the information providing unit 100A acquires a steering angle as the traveling state data from the steering angle sensor 3.

In step S1030, the information providing unit 100A determines a learning situation. In this embodiment, the traveling time from the start of collection of data is used to determine the learning situation. A degree of learning SD may be calculated using the number of data pieces collected.

Specifically, in step S1030, the information providing unit 100A calculates the degree of learning SD on the basis of the following expression.

$$\text{Degree of learning } SD = \text{traveling time (s)}/(\text{time range} \times \text{coefficient})$$

Traveling time: time after traveling
Time range: time range (for example, 2000 seconds) of a traveling state distribution
Coefficient: coefficient (for example, 5) associated with a convergence time The value of (time range×coefficient) corresponds to a predetermined learning time.

The traveling time is acquired from the timer 50.

In step SI030, the information providing unit 100A then determines a learning situation from the calculated degree of learning SD.

In this embodiment, when the degree of learning SD is equal to or more than "1", it is determined that the learning situation is a learning-completed situation. On the other hand, when the degree of learning SD is less than "1", it is determined that the learning situation is a learning-uncompleted situation.

In step S1040, the information providing unit 100A determines an instability calculating method on the basis of the learning situation determined in step S1030. Specifically, the information providing unit 100A performs the process of step S1050 when it is determined that the learning situation is a learning-completed situation (the degree of learning SD≥1). On the other hand, the information providing unit 100A performs the process of step S1070 when it is determined that the learning situation is a learning-uncompleted situation (the degree of learning SD<1).

When it is determined that the learning is completed and the process progresses to step S1050, the information providing unit 100A calculates plural driving traveling state distributions using a steering entropy method and calculates a difference value (relative entropy) between the distributions. Thereafter, the process progresses to step S1060.

Specifically, in step S1050, the information providing unit 100A calculates the difference value for determining how the driver's current driving operation is different from the normal driving operation, i.e., whether the current driving operation is unstable in comparison with the normal driving operation, on the basis of the steering angle when the driver performs a steering operation. That is, in step S1050, relative entropy (feature amount, instability) is calculated as a value indicating a disorder that is an unsmooth driving operation. In general, in a state where a driver does not pay attention to the driving operation, the time in which the steering is not performed is longer than that of the normal driving operation in which the driver pays attention to the driving, and thus a large steering angle error is accumulated. Therefore, the corrected steering amount when the driver pays attention to the driving again increases. In this embodiment, the relative entropy RHp is calculated using this characteristic. Specifically, a steering error distribution (traveling state distribution) accumulated in the past or for a long time previous to the current and a driver's steering error distribution (traveling state distribution) in the current time acquired for a short time, i.e., plural traveling state distributions of different time ranges, are calculated. With the steering error distribution for a long time which is considered as the normal driving characteristics as a comparison reference, the relative entropy RHp is calculated based on the long-time steering error distribution and the current short-time steering error distribution.

Here, the relative entropy RHp is a physical quantity indicating a difference value (distance) between the two steering error distributions and represents the degree of difference between the two steering error distributions, i.e., by what the two steering error distributions depart from each other. The stability of the current immediately-previous traveling state relative to the past long-time traveling state (normal driving characteristics) can be evaluated using the calculated value of relative entropy.

An example of calculating the steering error distribution accumulated for a long time, the driver's current steering error distribution acquired for a short time, and the difference value (relative entropy) between the distributions will be described later.

In step S1060, the information providing unit 100A determines an unstable driving state on the basis of the difference value.

In step S1060 of this embodiment, the difference value calculated in step S1050 is compared with a predetermined threshold value for determination. When the difference value is larger than the threshold value for determination, it is determined that the driving state is unstable. Thereafter, the process progresses to step S1100.

On the other hand, when it is determined in step S1040 that the learning is not completed, the process progresses to step S1070.

In step S1070, the information providing unit 100A calculates a current feature amount (absolute entropy) using the current steering error distribution of the shorter time range. Thereafter, the process progresses to step S1080. The absolute entropy is an expected value appearing in the subject traveling state distribution.

In step S1080, the information providing unit 100A reads the past driving feature amount. The past driving feature amount is the final value (absolute entropy) at the time of traveling in the past. Thereafter, the process progresses to step S1090.

In step S1090, the information providing unit 100A compares the current feature amount Hp_current calculated in step S1070 with the reference feature amount obtained by multiplying the past driving feature amount Hp_old read in step S1080 by a coefficient k, as expressed in the following expression. When the current feature amount Hp_current is larger than the reference feature amount (Hp_old*k), it is determined that the traveling state is unstable. Thereafter, the process progresses to step S1100.

$$Hp\_current/(Hp\_old*k)>1$$

Here, the coefficient k is set to, for example, 1.5.

In step S1100, the information providing unit 100A performs an information presenting process when it is determined in step S1060 or step S1090 that the traveling state is unstable.

An example of information to be presented is shown in FIGS. 4A and 4B. That is, when the degree of learning SD is equal to or more than "1" and it is determined that the traveling state is unstable, the information presenting device displays a warning as shown in FIG. 4A and presents a warning voice such as "Driving is disturbed. Please drive with attention!".

On the other hand, when the degree of learning SD is less than "1" and it is determined that the traveling state is unstable, the estimation accuracy may be low and thus the information presenting device presents a warning voice in a kind of gentle expression such as "How are your condition? Please, continuously drive safely!".

In this way, the information to be provided is changed depending on the degree of learning SD.

In step S1110, the current feature amount (absolute entropy) is stored. The current feature amount (the feature amount calculated in step S1070) is stored for comparison in the next trip (traveling).

Thereafter, the process is terminated and returns.

An example of a process of calculating the steering error distribution (traveling state distribution) accumulated for a long time, the driver's current steering error distribution (traveling state distribution) acquired for a short time, and the difference value (relative entropy) between the distributions will be described with reference to FIG. 5.

Details of this process are continuously performed at a constant interval, for example, every 50 msec.

In step S10, a traveling scene of the vehicle is estimated (detected) to determine whether the traveling scene is a traveling scene in which the relative entropy RHp is calculable. Here, when a vehicle velocity V lies within a predetermined vehicle velocity range (for example, 40 km/h to 120 km/h), it is determined that the traveling scene is a traveling scene in which the relative entropy RHp is calculable. That is, a case where the vehicle velocity is extremely slow and a case where the vehicle velocity is extremely fast are excluded from the calculable traveling scene so as to effectively calculate the relative entropy RHp using a steering angle signal.

In step S20, it is determined whether the current vehicle velocity V detected by the vehicle velocity sensor 4 lies within a predetermined vehicle velocity range. When it is determined that the vehicle velocity V lies within the predetermined vehicle velocity range and the traveling scene is a traveling scene in which the relative entropy RHp is calculable, the process progresses to step S30 so as to calculate the relative entropy RHp. On the other hand, when it is determined that the vehicle velocity V does not lie within the predetermined range, the process is terminated.

In step S30, a current steering angle signal θ detected by the steering angle sensor is read as a driver's driving operation amount to be detected to detect the driver's unstable driving state. In step S31, a steering angle prediction error θe is calculated based on the read value of the steering angle signal θ.

Figures 5, 6:
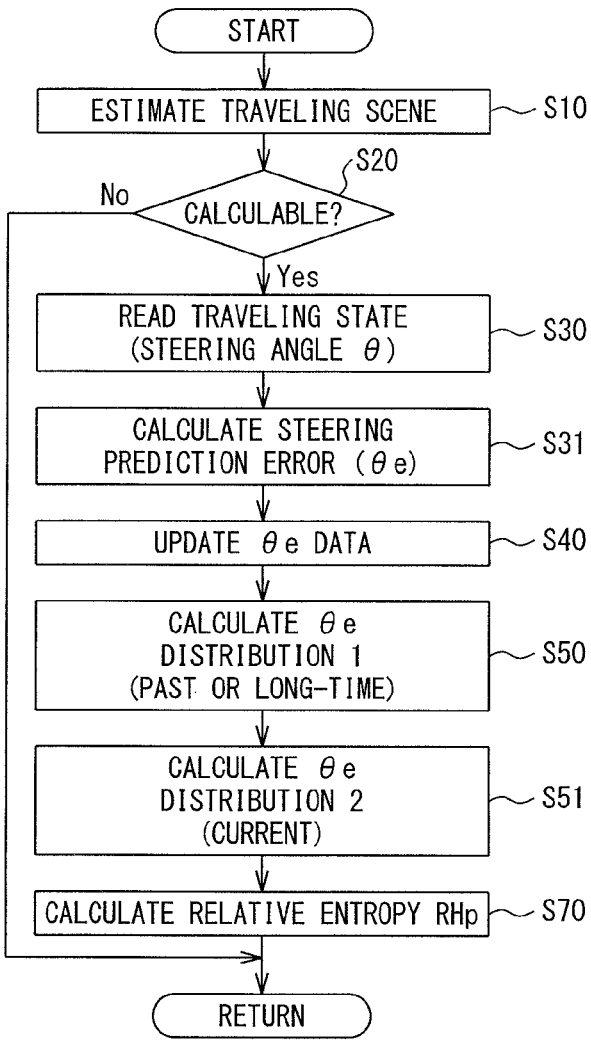
FIG. 5 is a diagram illustrating an example of calculating relative entropy.
FIG. 6 is a diagram illustrating signs used to calculate relative entropy.

Here, special signs and names thereof used to calculate the relative entropy RHp are shown in FIG. 6. A smoothed steering angle value θn-tilde is a steering angle from which the influence of quantization noise is reduced. An estimated steering angle value θn-hat is a value obtained by estimating the steering angle at the time of sampling on the assumption that the steering is smoothly carried out. As expressed by Expression 1, the estimated steering angle value θn-hat is acquired by performing a second-order Taylor expansion process on the smoothed steering angle value θn-tilde.

"Math 1"

$$\hat{\theta}_n = \tilde{\theta}_{n-1} + (t_n - t_{n-1})\left(\frac{\tilde{\theta}_{n-1} - \tilde{\theta}_{n-2}}{t_{n-1} - t_{n-2}}\right) + \frac{(t_n - t_{n-1})}{2}\left(\frac{\tilde{\theta}_{n-1} - \tilde{\theta}_{n-2}}{t_{n-1} - t_{n-2}} - \frac{\tilde{\theta}_{n-2} - \tilde{\theta}_{n-3}}{t_{n-2} - t_{n-3}}\right)$$

(Expression 1)

In Expression 1, to represents the sampling time of the steering angle θn.

The smoothed steering angle value θn-tilde is calculated as an average value of three neighboring steering angles θn in accordance with Expression 2 so as to reduce the influence of quantization noise.

"Math 2"

$$\tilde{\theta}_{n-k} = \frac{1}{3}\sum_{i=-l}^{l}\theta_{n-kl+i}$$

(Expression 2)

In Expression 2, l represents the number of samples of the steering angles θn included in 150 msec when the calculation time interval of the smoothed steering angle value θn-tilde is set to 150 msec, i.e., the minimum time interval which a human being can intermittently manipulate in a manual operation.

When the sampling interval of the steering angle θn is defined as Ts, the number of samples l is expressed by Expression 3.

$$l = \text{round}(0.15/Ts)$$

(Expression 3)

In Expression 2, k has values of 1, 2, and 3, and the smoothed value θn-tilde can be calculated using (k*l) on the basis of three steering angles θn as sum of the steering angles at the intervals of 150 msec and neighboring steering angles adjacent thereto. Therefore, the estimated value θn-hat calculated on the basis of the smoothed value θn-tilde is substantially calculated based on the steering angle θ obtained at the intervals of 150 msec.

The steering angle prediction error θe at the time of sampling can be calculated by Expression 4 as a difference between the estimated steering angle value θn-hat when it is assumed that the steering operation is smoothly carried out and an actual steering angle value θn.

"Math 3"

$$\theta e = \theta n - \hat{\theta} n$$

(Expression 4)

Here, the steering angle prediction error θe is calculated for the steering angle θn every the minimum time interval, i.e., 150 msec, which a human being can intermittently manipulate.

A specific method of calculating the steering angle prediction error θe will be described below. The sampling interval Ts of the steering angle signal θ is set to, for example, 50 msec. First, three smoothed steering angle values θn-tilde are calculated in accordance with Expression 2 using three neighboring steering angles θn with an interval of 150 msec. The three smoothed steering angle values θn-tilde are expressed by Expression 5.

"Math 4"

$$\tilde{\theta}_{n-1} = \frac{1}{3}(\theta_{n-4} + \theta_{n-3} + \theta_{n-2}),$$

$$\tilde{\theta}_{n-2} = \frac{1}{3}(\theta_{n-7} + \theta_{n-6} + \theta_{n-5}),$$

$$\tilde{\theta}_{n-3} = \frac{1}{3}(\theta_{n-10} + \theta_{n-9} + \theta_{n-8}),$$

(Expression 5)

The estimated steering angle values θn-hat are calculated in accordance with Expression 1 using the calculated three smoothed steering angle values θn-tilde. The estimated values θn-hat are expressed by Expression 6.

"Math 5"

$$\hat{\theta}_n = \tilde{\theta}_{n-1} + Ts \cdot \frac{\tilde{\theta}_{n-1} - \tilde{\theta}_{n-2}}{Ts} + \frac{Ts}{2}\left(\frac{\tilde{\theta}_{n-1} - \tilde{\theta}_{n-2}}{Ts} - \frac{\tilde{\theta}_{n-2} - \tilde{\theta}_{n-3}}{Ts}\right)$$

$$= \tilde{\theta}_{n-1} + (\tilde{\theta}_{n-1} - \tilde{\theta}_{n-2}) + \frac{1}{2}[(\tilde{\theta}_{n-1} - \tilde{\theta}_{n-2}) - (\tilde{\theta}_{n-2} - \tilde{\theta}_{n-3})]$$

(Expression 6)

The steering prediction error θe is calculated in accordance with Expression 4 using the calculated estimated steering angle values θn-hat and the actual steering angle θn.

In step S40, data of the steering angle prediction error θe for a predetermined time of T seconds which is calculated up to now and stored in the memory of the controller 100 is updated by adding the current value of the steering angle prediction error θe calculated in step S31 thereto. That is, the earliest data before T seconds out of the accumulated data of the steering angle prediction error θe is deleted and the current value calculated in step S31 is input instead as the latest data of the steering angle prediction error θe. Accordingly, the data of the steering angle prediction error θe before T seconds from the current value is accumulated. The predetermined time T is set to, for example, T=3600 seconds (=1 hour) so as to accumulate long-period data sufficient to calculate a long-time error distribution which is a comparison reference for determining the unstable state of the current driving operation.

Figure 7:
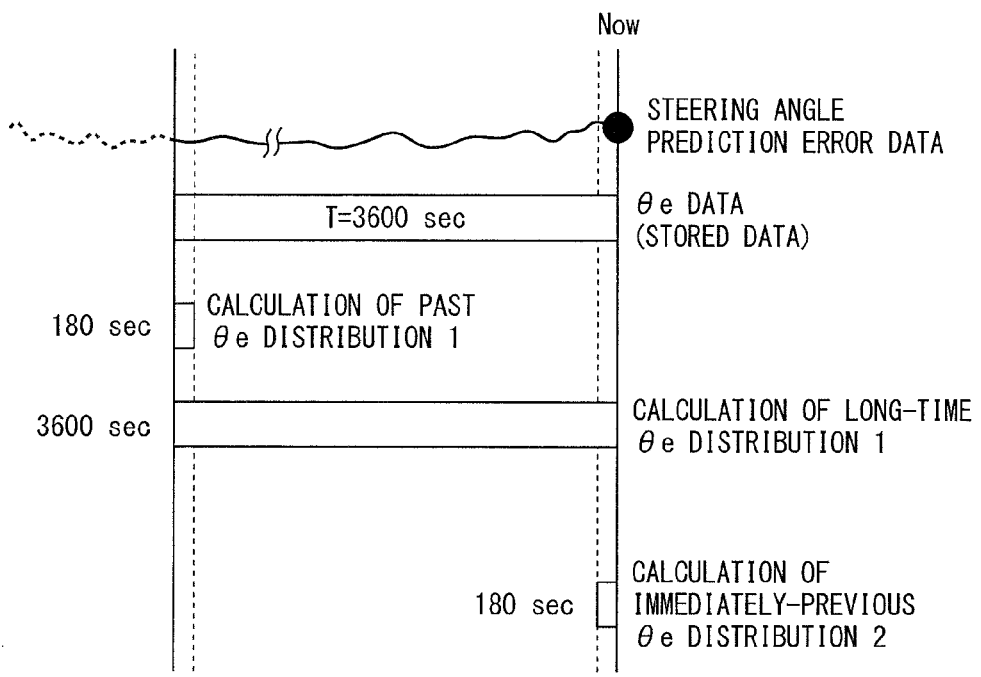
FIG. 7 is a diagram illustrating a method of calculating a past or long-time distribution and an immediately-previous distribution based on steering angle prediction error data.

In step S50, past or long-time steering angle prediction error distribution 1 is calculated which serves as the comparison reference of the steering angle prediction error distribution. Here, as shown in FIG. 7, the past steering angle prediction error distribution is calculated, for example, using data of 180 seconds based on the data before T seconds. Specifically, the accumulated past steering angle prediction error θe is classified into nine prediction error sections b1 to b9 and the probability pi (=p1 to p9) of the frequency of the steering angle prediction error θe included in each section bi with respect to the total frequency is calculated. The calculated past distribution is used as the comparison reference of the steering angle prediction error distribution. The range of the prediction error section bi is set in advance so as to be constant in all the sections b1 to b9.

When the long-time steering angle prediction error distribution is calculated, all data of 3600 seconds from before T seconds to the current time are used. Specifically, the accumulated long-time steering angle prediction error θe is classified into nine prediction error sections b1 to b9 and the probability pi (=p1 to p9) of the frequency of the steering angle prediction error θe included in each section bi with respect to the total frequency is calculated. The calculated past distribution (or long-time distribution) is used as a Past (or long-time) steering angle prediction error distribution 1 serving as the comparison reference.

In step S51, a current steering angle prediction error distribution 2 is calculated. Here, as shown in FIG. 7, the current steering angle prediction error distribution 2 is calculated using immediately-previous data of 180 seconds from the current time. Specifically, the data of the steering angle prediction error θe of immediately-previous 180 seconds is classified into nine prediction error sections b1 to b9 and the probability qi (=q1 to q9) of the frequency of the steering angle prediction error θe included in each section bi with respect to the total frequency is calculated.

Figure 8:
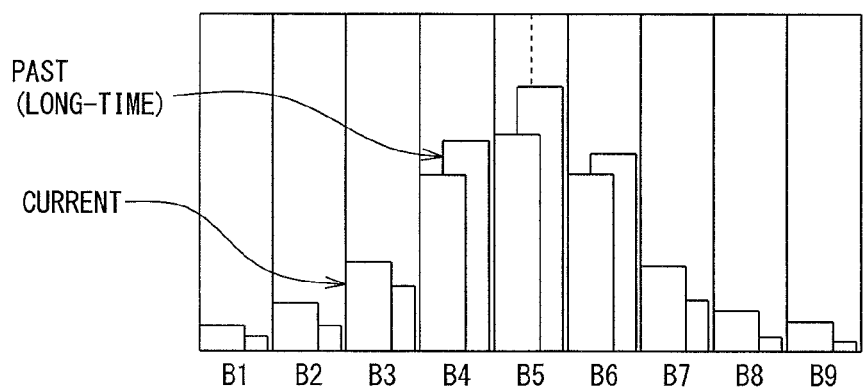
FIG. 8 is a diagram illustrating a method of calculating relative entropy.

In step S70, the relative entropy RHp is calculated using past (or long-time) steering angle prediction error distribution 1 and current steering angle prediction error distribution 2. As shown in FIG. 8, the relative entropy RHp is a difference value (distance) between current steering angle prediction error distribution 2 and past (or long-time) steering angle prediction error distribution 1 as the comparison reference. The relative entropy RHp can be calculated using Expression 7.

"Math 6"

$$RHp = \sum q_i \cdot \log_9 \frac{q_j}{p_i}$$ (Expression 7)

The relative entropy RHp becomes RHp=0 when the probability pi of the past (or long-time) steering angle prediction error distribution 1 and the probability qi of the current steering angle prediction error distribution 2 are equal to each other, and the value of RHp increases when the probabilities pi and qi are more different from each other.

Then, this process is terminated. The above-mentioned process is performed repeatedly.

The range of the prediction error section bi for calculating the past (or long-time) steering angle prediction error distribution 1 and the current steering angle prediction error distribution 2 may be set on the basis of an α value used to calculate steering entropy Hp indicating ambiguity (uncertainty) of the steering error distribution. Here, the α value is calculated as a 90 percentile (a range of distribution including 90% of the steering error) by calculating the steering error within a constant time, i.e., the difference between the estimated steering angle value and the actual steering angle when it is assumed that the steering operation is smoothly carried out, on the basis of time-series data of the steering angle and measuring a distribution (deviation) of the steering error.

Figures 9, 10:
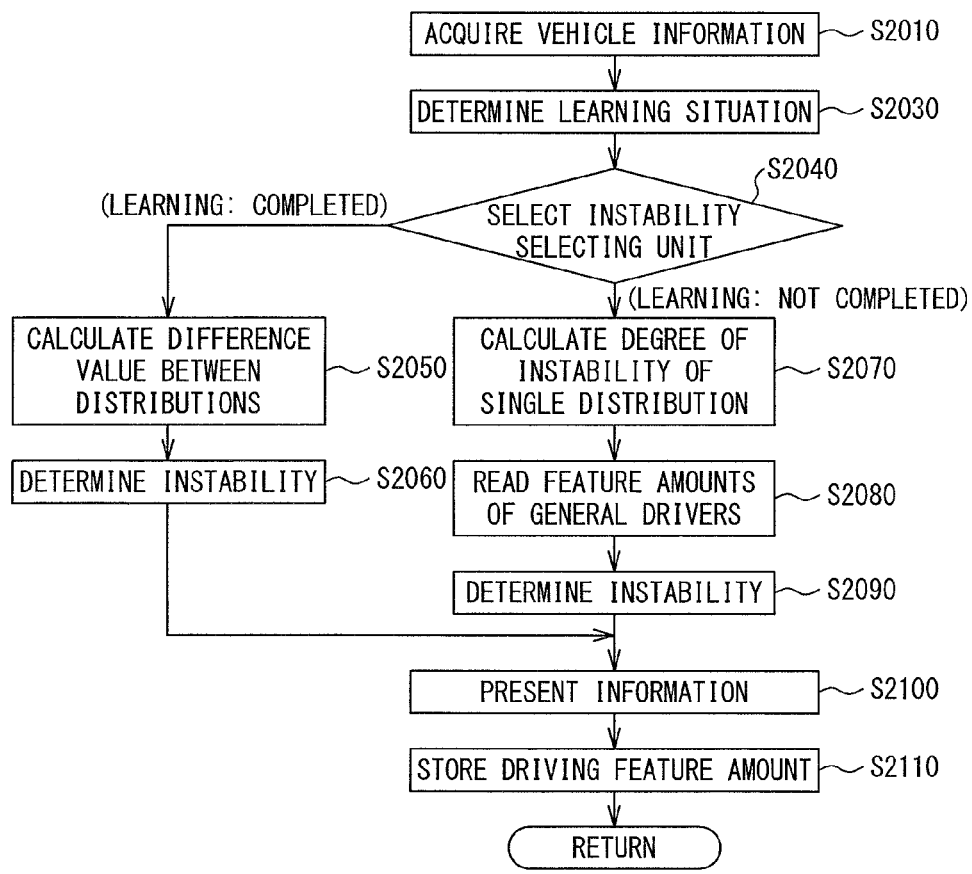
FIG. 9 is a diagram illustrating sections of a steering angle prediction error.
FIG. 10 is a diagram illustrating a process in an information providing unit according to a second embodiment of the present invention.

Therefore, the α value is calculated on the basis of the past (or long-time) steering angle prediction error distribution and the same range of the prediction error sections bi is set for past (or long-time) steering angle prediction error distribution 1 and current steering angle prediction error distribution 2 using the calculated α value. FIG. 9 shows the ranges of the steering angle prediction error θe of the sections bi set using the α value.

(Operation and the Other)

When a learning situation can be considered as a learning-completed situation (that the normal driving characteristics of a driver can be acquired) on the basis of the traveling time after collection of data starts, the information provision device for use in a vehicle calculates instability using a steering entropy method through the use of processes of steps S1050 and S1060.

At this time, the information provision device for use in a vehicle calculates the difference value between plural traveling state distributions calculated and determines the unstable driving state on the basis of the magnitude of the difference value. Accordingly, it is possible to accurately detect an unstable traveling state regardless of a variation in traffic environment. That is, it is possible to accurately detect an unstable state depending on the normal characteristics of a driver regardless of a variation in traffic environment.

At this time, the information provision device for use in a vehicle calculates plural traveling state distributions of different time ranges as plural traveling state distributions. For example, the information provision device for use in a vehicle calculates a traveling state distribution including past traveling state data and a traveling state distribution including immediately-previous traveling state data, and directly calculates the difference of the immediately-previous traveling state distribution on the basis of the past traveling state distribution. As a result, it is possible to evaluate stability of an immediately-previous state while continuously updating reference data. In this way, it is possible to accurately detect an unstable traveling state regardless of a variation in traffic environment.

On the other hand, when it is determined that the learning situation is a learning-uncompleted situation (SD<1), the information provision device for use in a vehicle compares the past traveling data with the magnitude of the single traveling state distribution which is the traveling state distribution of the immediately-previous time range indicating the current traveling state and determines an unstable driving state (steps S1070 to S1090). That is, by using a different instability calculating process at the time of incompletion of learning, it is possible to attract attention even when the traveling state distribution of a driver is not known.

In the above-mentioned embodiment, the degree of learning SD is calculated using the traveling time, it is estimated whether it can be estimated that the traveling state distribution is matched with the driving characteristics of a driver on the basis of the degree of learning SD, and it is thus determined whether the learning is completed. The degree of learning SD used to estimate that the traveling state distribution is matched with the driving characteristics of a driver may be calculated based on a variation in the relative entropy which is a feature amount of the traveling state distribution. For example, when the variation in the feature amount of the long-time traveling state distribution is equal to or less than a predetermined value, a value indicating the completion of learning is set as the degree of learning SD.

Here, step S1010 constitutes the traveling state acquiring unit. Step S1050 constitutes the first traveling state distribution calculating unit and the first driving instability determining unit. Step S1030 constitutes the learning terminal determining unit. Steps S1070 and S1080 constitute the second driving instability determining unit. Step S1040 constitutes the instability selecting unit. Step S1100 constitutes the information presenting unit.

(Advantages of this Embodiment)

(1) The traveling state acquiring unit acquires traveling state data including at least one of a driving operation of a driver and a vehicle state. The first traveling state distribution calculating unit calculates plural traveling state distributions of different time ranges on the basis of the traveling state data acquired by the traveling state acquiring unit. The first driving instability determining unit estimates driving instability on the basis of a difference value between plural traveling state distributions calculated by the first traveling state distribution calculation unit. The learning completion determining unit determines that learning is completed when a predetermined learning time elapses from the start of collection of the traveling state data, on the basis of the degree of learning SD which is a degree at which the traveling state distribution calculated by the first traveling state distribution calculating unit is matched with the driving characteristics of a driver. The degree of learning SD is calculated as a degree at which the traveling state distribution calculated by the first traveling state distribution calculating unit is matched with the driving characteristics of a driver. The second driving instability determining unit estimates driving instability by comparing a comparative traveling state distribution acquired on the basis of another traveling state data different from the traveling state data of the immediately-previous time range, with the traveling state distribution of the immediately-previous time range, which indicates the current traveling state and calculated on the basis of the traveling state data acquired by the traveling state acquiring unit. The instability selecting unit selects the instability estimated by the first driving instability determining unit when the learning is completed and selects the instability estimated by the second driving instability determining unit when the learning is completed, on the basis of the determination result of the learning completion determining unit. The information presenting unit presents instability information based on the instability selected by the instability selecting unit to the driver.

By employing a different instability calculating unit at the time of incompletion of learning, it is possible to attract attention even when the traveling state distribution of a driver is not known.

(2) The another traveling state data is traveling state data acquired prior to the immediately-previous time range. The second driving instability determining unit compares the comparative traveling state distribution with the traveling state distribution of the immediately-previous time range by the use of a ratio of a feature amount of the traveling state distribution of the immediately-previous time range and a reference feature amount, which is a value obtained by multiplying a feature amount of the traveling state distribution acquired from the another traveling state data by a predetermined coefficient, and estimates the driving instability.

By calculating the reference feature amount by multiplying the feature amount of the traveling state distribution calculated from the different traveling data by the predetermined coefficient, it is possible to improve the estimation accuracy of the driving instability through the correction using the coefficient even when the learning is not completed.

(3) The second driving instability determining unit estimates the driving instability on the basis of at least one of information of the traveling state data acquired by the traveling state acquiring unit and driving scene information of the vehicle.

By using the vehicle behavior data, other traveling state data, and the determination result of a driving scene, it is possible to accurately detect a driver's driving state.

(4) The second driving instability determining unit estimates the driving instability using one of the traveling state distributions calculated on the basis of the traveling state data acquired by the traveling state acquiring unit.

By using the traveling state distribution of a driver, it is possible to enable a statistical process and thus to improve accuracy.

(5) When the instability selecting unit selects the instability estimated by the second driving instability determining unit and the instability estimated by the second driving instability determining unit is greater than a predetermined threshold value for determination, it is determined that the driving state is unstable.

Accordingly, it is possible to simply determine the unstable driving state.

(6) The threshold value for determination is set on the basis of data of a past traveling history.

By using the past traveling history, it is possible to improve the detection accuracy.

(7) The second driving instability determining unit includes a history storage unit that stores the data of the past traveling history and determines the unstable state with reference to the tendency of the past history stored in the history storage unit.

The determination using the past history improves the detection performance.

(8) The learning completion determining unit determines the degree of learning SD using the traveling time.

By determining the learning situation using the traveling time, it is possible to reduce erroneous determination of the completion of learning.

(9) The learning completion determining unit determines the completion of learning using the variation in the feature amount of a single traveling state distribution.

By determining the learning situation based on the variation in the feature amount of the traveling state distribution, it is possible to determine the completion of learning promptly.

(10) The traveling state distribution is calculated based on the operation amount of a steering operation.

By detecting the traveling state distribution based on the steering operation requiring a continuous operation, it is possible to accurately detect the driving state.

(11) A steering entropy method is used to calculate the traveling state distribution based on the operation amount of the steering operation.

By using the steering entropy method, it is possible to improve the detection performance.

(12) The information presenting unit changes the instability information to be presented depending on the learning completion result determined by the learning completion determining unit.

By changing the information to be presented depending on the determination result of the completion of learning, it is possible to improve the acceptability of a driver.

Second Embodiment

A second embodiment will be described below with reference to the accompanying drawings. The same elements as in the first embodiment will be referenced by the same reference signs.

The basic configuration of this embodiment is the same as in the first embodiment. Both are different from each other, in the different instability calculating process performed when the learning situation is determined to be a learning uncompleted situation.

In this embodiment, the different instability calculating process is performed by comparing the magnitude of a single traveling state distribution with a value calculated based on distributions of general drivers and determining whether the driving state is unstable.

The process in an information providing unit 100A according to this embodiment will be described below with reference to the flow chart of FIG. 10.

Here, the processes of steps S2010 to S2070 are the same as the processes of steps S1010 to S1070 in the first embodiment. The processes of steps S2100 and S2110 are the same as the processes of steps S1100 and S1110. Accordingly, such processes will not be described again.

The process of step S2080 will be described below.

In step S2080 in this embodiment, the information providing unit 100A reads feature amounts of general drivers stored in advance in a storage unit.

The feature amounts of general drivers are values obtained by performing a statistical process (for example, averaging) on the feature amounts acquired from plural drivers in advance. The feature amounts of the general drivers may be appropriately updated through wireless communications or the like. The feature amounts acquired from the drivers are calculated from the traveling state data acquired from the drivers.

The other processes are the same as in the first embodiment.

Here, step S2010 constitutes the traveling state acquiring unit. Step S2050 constitutes the first traveling state distribution calculating unit and the first driving instability determining unit. Step S2030 constitutes the learning terminal determining unit. Steps S2070 and S2080 constitute the second driving instability determining unit. Step S2040 constitutes the instability selecting unit. Step S2100 constitutes the information presenting unit.

(Operational Advantages)

In this embodiment, the following advantages can be obtained in addition to the advantages described in the first embodiment.

(1) The another traveling state data used in the second driving instability determining unit is traveling state data acquired in advance from plural drivers. The threshold value for determination is acquired from the characteristics of the traveling state distributions acquired from the plural drivers.

By using the distributions serving as a reference of general drivers, it is possible to clarify the unstable state of a driver and thus to improve the detection performance.

Third Embodiment

A third embodiment will be described below with reference to the accompanying drawings. The same elements as in the first embodiment will be referenced by the same reference signs.

The basic configuration of this embodiment is the same as in the first embodiment. In the third embodiment, the different process of calculating a degree of instability when the learning situation is determined to be a learning-uncompleted situation is performed on the basis of the history of the feature amount of a single distribution acquired based on the traveling state of the immediately-previous time range.

Figure 11:
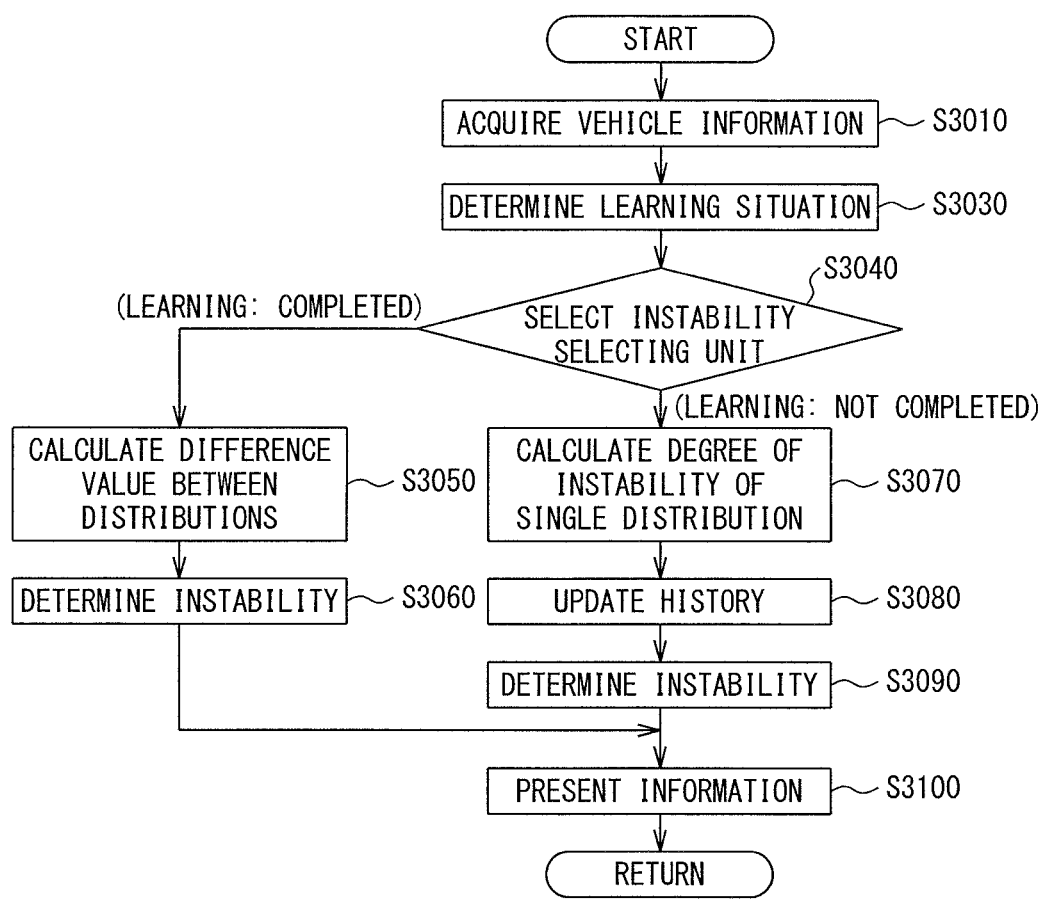
FIG. 11 is a diagram illustrating a process in an information providing unit according to a third embodiment of the present invention.

The process in an information providing unit 100A according to this embodiment will be described below with reference to the flow chart of FIG. 11.

The processes of steps S3010 to S3070 are the same as the processes of steps S1010 to S1070 in the first embodiment. The process of steps S3100 is the same as the process of steps S1100. Accordingly, such processes will not be described again. Since it is not necessary to store the feature amount in this embodiment, the process of step S1110 is not performed.

The processes of steps S3080 and S3090 in this embodiment will be described below.

In step S3080 of this embodiment, the information providing unit 100A stores several to ten pieces of instability calculated in step S3070 at constant intervals and calculates a deviation, a variation, and an absolute value so as to determine the tendency thereof.

The deviation is a deviation (standard deviation) of the past instability.

The variation is based on the comparison of the earliest instability with the latest instability.

The absolute value is an absolute value of the latest instability.

In step S3090, the information providing unit 100A determines the past history data calculated in step S3080.

For example, when the above-mentioned three items (deviation, variation, and absolute value) satisfy the conditions of a large deviation, a great variation, and a large absolute value, it is determined that the driving state is unstable. When same conditions of the three items satisfy the conditions, for example, when any one condition is satisfied, it may be determined that the driving state is unstable.

Here, when the deviation is larger than a predetermined threshold value for deviation, it is determined that the deviation is large. When the absolute value of the variation is larger than a predetermined threshold value for variation, it is determined that the variation is greater. When the absolute value is larger than a predetermined threshold value for absolute value, it is determined that the absolute value is large.

The other processes are the same as in the first embodiment.

Here, step S3010 constitutes the traveling state acquiring unit. Step S3050 constitutes the first traveling state distribution calculating unit and the first driving instability determining unit. Step S3030 constitutes the learning terminal determining unit. Steps S3070 and S3080 constitute the second driving instability determining unit. Step S3040 constitutes the instability selecting unit. Step S3100 constitutes the information presenting unit.

(Operational Advantages)

As described above, in this embodiment, the feature amount (entropy) of a single traveling state distribution is appropriately stored and the unstable driving is determined on the basis of the tendency (the variation and the absolute value) thereof.

In this embodiment, the following advantages can be obtained in addition to the advantages described in the first embodiment.

(1) The second driving instability determining unit calculates the feature amount of the traveling state distribution of the immediately-previous time range indicating the current traveling state based on the traveling state data acquired by the traveling state acquiring unit, and estimates the degree of instability of the driving on the basis of the calculated feature amount.

By using the feature amount of the traveling state distribution of a driver, it is possible to perform a statistical process and thus to improve the accuracy.

(2) The second driving instability determining unit calculates the tendency of the feature amount on the basis of the history of the feature amount acquired every constant interval, and estimates the degree of driving instability on the basis of the calculated tendency.

According to this configuration, by using the tendency of the feature amount, it is possible to determine unstable driving without using the traveling state distribution of a long-time time range.

Fourth Embodiment

A fourth embodiment will be described below with reference to the accompanying drawings. The same elements as in the first embodiment will be referenced by the same reference signs.

The basic configuration of this embodiment is the same as in the first embodiment. In the fourth embodiment, the different process of calculating a degree of instability when the learning situation is determined to be a learning-uncompleted situation is performed on the basis of the relative entropy values of different time ranges.

Figure 12:
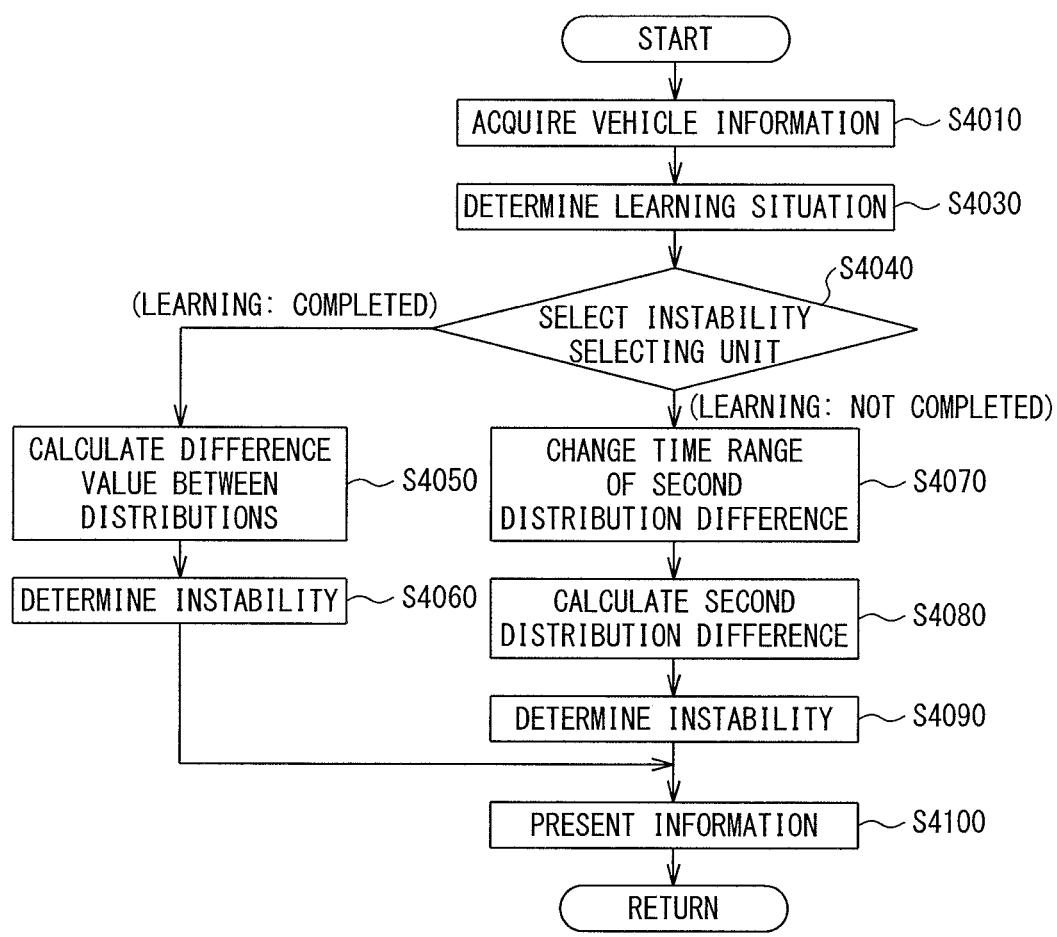
FIG. 12 is a diagram illustrating a process in an information providing unit according to a fourth embodiment of the present invention.

The process in an information providing unit 100A according to this embodiment will be described below with reference to the flow chart of FIG. 12.

The processes of steps S4010 to S4060 are the same as the processes of steps S1010 to S1060 in the first embodiment. The process of steps S4100 is the same as the process of steps S1100. Accordingly, such processes will not be described again. Since it is not necessary to store the feature amount in this embodiment, the process of step S1110 is not performed.

The processes of steps S4070 and S4090 will be described below.

In step S4030, the learning situation is determined as described above.

The learning situation is determined using the traveling time as described above. The degree of learning SD is calculated, for example, using the following expression.

Degree of learning $SD$=traveling time (s)/(time range×coefficient)

Traveling time: time after traveling
Time range: time range (for example, 2000 seconds) of a traveling state distribution
Coefficient: coefficient (for example, 5) associated with a convergence time In step S4070, the information providing unit 100A sets the time ranges in which two steering error distributions (traveling state distributions) are calculated depending on the degree of learning SD calculated in step S4030. In this embodiment, the two traveling state distributions include a long traveling time distribution and a short traveling time distribution. The time range of the long traveling time distribution is set to the time range based on the degree of learning SD as described below. The short traveling state distribution is calculated as described above.

Time range of long-time traveling time distribution=degree of learning $SD$×learning coefficient Degree of learning: value (0 to 1) calculated in step S4030
Learning coefficient: learning time or a value obtained by multiplying the learning time by a predetermined coefficient (<1).

The learning coefficient is obtained, for example, by multiplying the learning time (traveling time) by a predetermined constant of 1 or less.

In step S4080, the information providing unit 100A calculates a second distribution difference. The calculation is performed in the same ways as in step S4050 (step S1050). Here, the time range thereof is different from that of the traveling state distribution for calculating a first distribution difference. The time range of the second traveling state distribution is narrower than the time ranges of the first traveling state distribution.

When the time ranges of the first traveling state distribution are set to Tw_s1 and Tw_l1 and the time ranges of the second first traveling state distribution are set to Tw_s2 and Tw_l2, these values are set as follows, for example.
Tw_s1: 60 (s)
Tw_l1: 2000 (s)
Tw_s2: 20 (s)
Tw_l2: 600 (s)

In step S4080, the information providing unit 100A prepares two traveling state distributions and calculates the difference therebetween, on the basis thereon.

In step S4090, the information providing unit 100A determines the unstable driving state on the basis of the difference (feature amount) calculated in step S4080. In step S4090 of this embodiment, the information providing unit 100A compares the difference calculated in step S4080 with a predetermined threshold value for determination. Then, the information providing unit 100A determines that the driving state is unstable when the difference is larger than the threshold value for determination. Thereafter, the process progresses to step S4100.

Here, step S4010 constitutes the traveling state acquiring unit. Step S4050 constitutes the first traveling state distribution calculating unit and the first driving instability determining unit. Step S4030 constitutes the learning terminal determining unit. Steps S4070 to S4090 constitute the second driving instability determining unit. Step S4070 constitutes the second traveling state distribution calculating unit and the second driving instability determining unit. Step S4040 constitutes the instability selecting unit. Step S4100 constitutes the information presenting unit.

(Operational Advantages)

In this embodiment, when the learning situation is determined to be a learning-uncompleted situation, the information providing unit 100A calculates two relative entropy values of different time ranges and changes the time range of one relative entropy value depending on the learning situation.

In this embodiment, the following advantages can be obtained in addition to the advantages of the first embodiment.

(1) The another traveling state data used in the second driving instability determining unit are traveling state data acquired in another time range different from the immediately-previous time range. The another time range is changed depending on the degree of learning as a ratio of the time elapsing from the start of collection of the traveling state data up to now to the learning time, and the another time range increases with an increase in the degree of learning.

By causing such another time range to increase as it gets closer to the completion of learning, it is possible to further smoothly change the information to be presented to a driver when the incompletion of learning is transitioned to the completion of learning. For example, it is possible to further smoothly change the attraction of attention when the incompletion of learning is transitioned to the completion of learning.

Fifth Embodiment

A fifth embodiment will be described below with reference to the accompanying drawings. The same elements as in the first embodiment will be referenced by the same reference signs.

The basic configuration of this embodiment is the same as in the first embodiment. In the fifth embodiment, the different process of calculating a degree of instability when the learning situation is determined to be a learning-uncompleted situation is performed on the basis of the feature amounts (relative entropy) of two single distributions.

Figure 13:
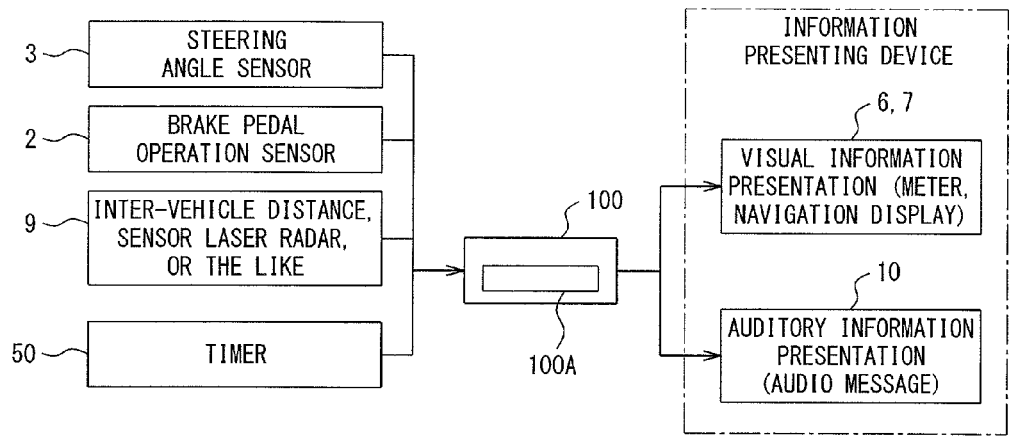
FIG. 13 is a diagram illustrating an example of a system configuration according to a fifth embodiment of the present invention.

The system configuration of this embodiment is shown in FIG. 13. As shown in FIG. 13, the outputs of the brake pedal operation amount sensor and an obstacle detecting device are input to the information providing unit 100A in addition to the outputs of the steering angle sensor 3 and the timer 50.

Figure 14:
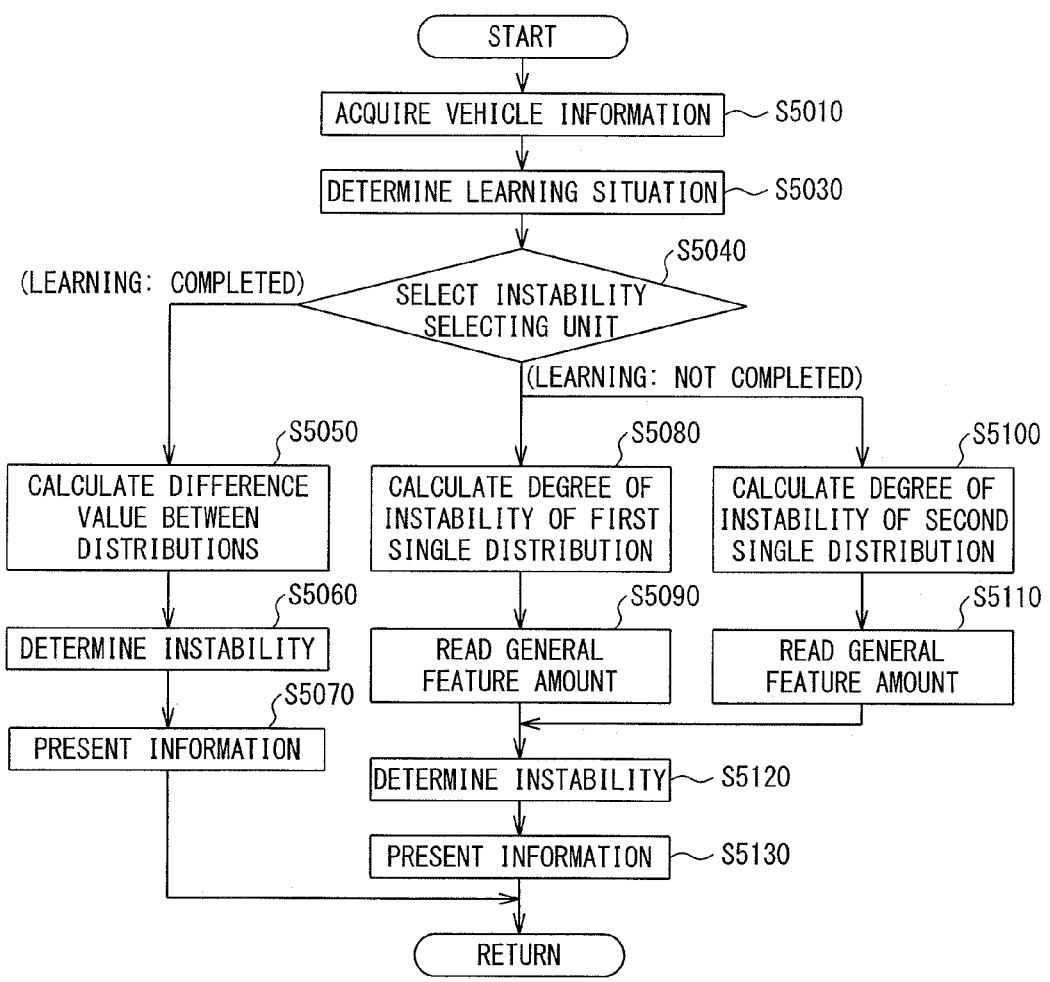
FIG. 14 is a diagram illustrating a process in an information providing unit according to the fifth embodiment of the present invention.

The process of the information providing unit 100A according to this embodiment will be described below with reference to the flowchart shown in FIG. 14.

First, in step S5010, the information providing unit 100A acquires the following data as vehicle information data.

The information providing unit 100A acquires a steering angle and a brake pedal operation amount as operation information of a driver on the basis of the outputs from the steering angle sensor 3 and the brake pedal operation amount sensor 2.

The information providing unit 100A acquires a vehicle velocity of the vehicle, a longitudinal G, a transverse G, a relative velocity to an obstacle ahead, and an inter-vehicle distance as information of a vehicle state on the basis of the outputs of the vehicle velocity sensor 4, the G sensor 8, and the vehicle ahead detecting device 9.

In step S5030, the information providing unit 100A determines a learning situation through the same process as in step S1050.

In step S5040, the information providing unit 100A determines whether the learning situation is a learning completed situation on the basis of the degree of learning SD through the same process as in step S1040. When the learning situation is determined to be a learning-completed situation, the process progresses to step S5050. On the other hand, when the learning situation is determined to be a learning-uncompleted situation, the process progresses to steps S5080 and S5100.

In steps S5050 and S5060, the same processes as in steps S1050 and S1060 are performed. That is, in step S5050, the difference value between the distributions is calculated. In step S5060, the calculated difference value is compared with a predetermined threshold value for determination and it is determined whether the driving state is unstable.

In step S5070, the information providing unit 100A performs an information presenting process when it is determined in step S5060 that the driving state is unstable.

On the other hand, in step S5080, the information providing unit 100A calculates a steering entropy value using the steering angle. In step S5080, the absolute entropy value (feature amount) as an instability value is calculated based on a single traveling state distribution. Thereafter, the process progresses to step S5090.

In step S5090, the information providing unit 100A performs the same process as in step S2080 and reads the feature amounts of general drivers stored in the storage unit. Thereafter, the process progresses to step S5120.

In step S5100, the information providing unit 100A calculates the absolute entropy value (feature amount) as an instability value based on the magnitude of the TTC (Time To Collision) at the time of braking. Thereafter, the process progresses to step S5110. Here, the time to collision (TTC) represents the time until colliding with an obstacle when the vehicle travels while maintaining the traveling state at the time of calculating the time to collision.

When the state of a driver is unstable, it is generally known that the braking timing is delayed. Therefore, it is possible to determine an unstable state by evaluating the braking timing. The braking timing is used after being normalized by using statistical data of a general braking operation.

For example, when the number of braking operations is N, it is assumed that TTC at the time of braking are defined as TTC1, TTC2, . . . . When the average value of general braking timing is defined as μ and the standard deviation thereof is defined as σ, the normalized values Std of the braking operations can be expressed as follows.

$$Std1 = (\mu - TTC1)/\sigma$$
$$Std2 = (\mu - TTC2)/\sigma$$
$$Std3 = (\mu - TTC3)/\sigma$$
$$...$$
$$Stdn = (\mu - TTCn)/\sigma$$

The average Std (ΣStdn (where n is a value of 1 to n)/N) is used as a degree of instability.

In step S5110, the information providing unit 100A reads an average value of TTC (a value set in advance in the storage unit) which is generally allowable. This value is set to, for example, a value between 2 and 3.

In step S5120, the information providing unit 100A determines that the driving state is unstable when any one of the first single distribution instability using the feature amount based on the processes of step S5080 and S5090 and the second single distribution instability using the feature amount based on the processes of steps S5100 and S5110 satisfies the following conditional expressions. When the following conditional expressions are satisfied, it is determined that the driving state is unstable.

Degree of instability calculated in step S5080>general feature amount read in step S5090

Degree of instability calculated in step S5100>general feature amount read in step S5110

In steps S5080 and S5100 of this embodiment, cases where the degree of instability is calculated based on the steering entropy and the TTC at the time of braking are exemplified, respectively. Instead, any of the driving operation of a driver and a vehicle behavior index (in addition, a frequency distribution of a transverse G and a longitudinal G) due to the driving operation may be used.

In step S5130, when it is determined in step S5120 that the driving state is unstable, the information providing unit 100A performs an information presenting process.

The other configurations are the same as in the first embodiment.

Here, step S5010 constitutes the traveling state acquiring unit. Step S5050 constitutes the first traveling state distribution calculating unit and the first driving instability determining unit. Step S5030 constitutes the learning terminal determining unit. Steps S5080 and S5120 constitute the second driving instability determining unit. Step S5040 constitutes the instability selecting unit. Steps S5070 and S5130 constitute the information presenting unit.

(Operational Advantages)

In this embodiment, the degree of instability is determined in consideration of other indices (such as the transverse G in right or left turn) in addition to the steering entropy. That is, two types of single traveling state distributions (which are calculated from different indices, respectively) are used and it is determined that the driving state is unstable when it is determined that any one thereof is unstable.

In this embodiment, the following advantages can be obtained in addition to the advantages described in the first embodiment.

(1) The another traveling state data used in the second driving instability determining unit is plural types of traveling state data. The second driving instability determining unit estimates each of plural traveling state distributions based on the plural types of traveling state data as comparative traveling state distributions respectively. That is, the second driving instability determining unit estimates the degree of driving instability from the feature amounts of plural traveling state distributions acquired from the plural types of traveling state data.

By detecting the state of a driver from plural signals as well as specific signals, it is possible to improve the detection performance.

(2) The second driving instability determining unit estimates the degree of driving instability using the time to collision (TTC).

By using the time to collision, it is possible to accurately detect a decelerating operation state.

Sixth Embodiment

A sixth embodiment will be described below with reference to the accompanying drawings. The same elements as in the first embodiment will be referenced by the same reference signs.

The basic configuration of this embodiment is the same as in the first embodiment. In the sixth embodiment, the different process of calculating a degree of instability when the learning situation is determined to be a learning-uncompleted situation is performed by calculating the feature amount of a specific driving scene.

Figure 15:
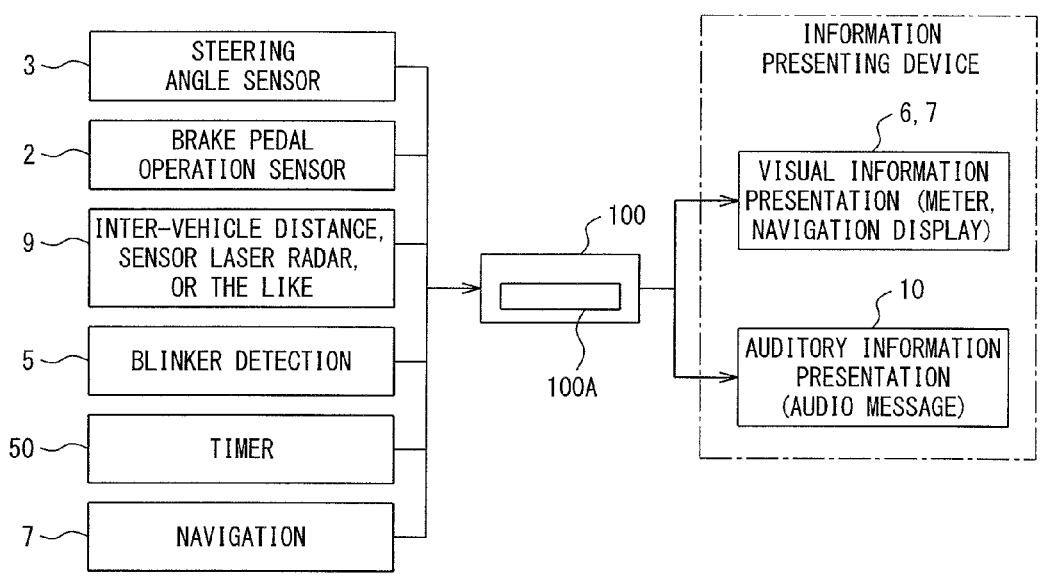
FIG. 15 is a diagram illustrating an example of a system configuration according to a sixth embodiment of the present invention.

FIG. 15 is a diagram illustrating a system configuration according to this embodiment. In this embodiment, intersection information is acquired through the use of a blinker indicating signal or a navigation system so as to detect a specific driving scene.

Figure 16:
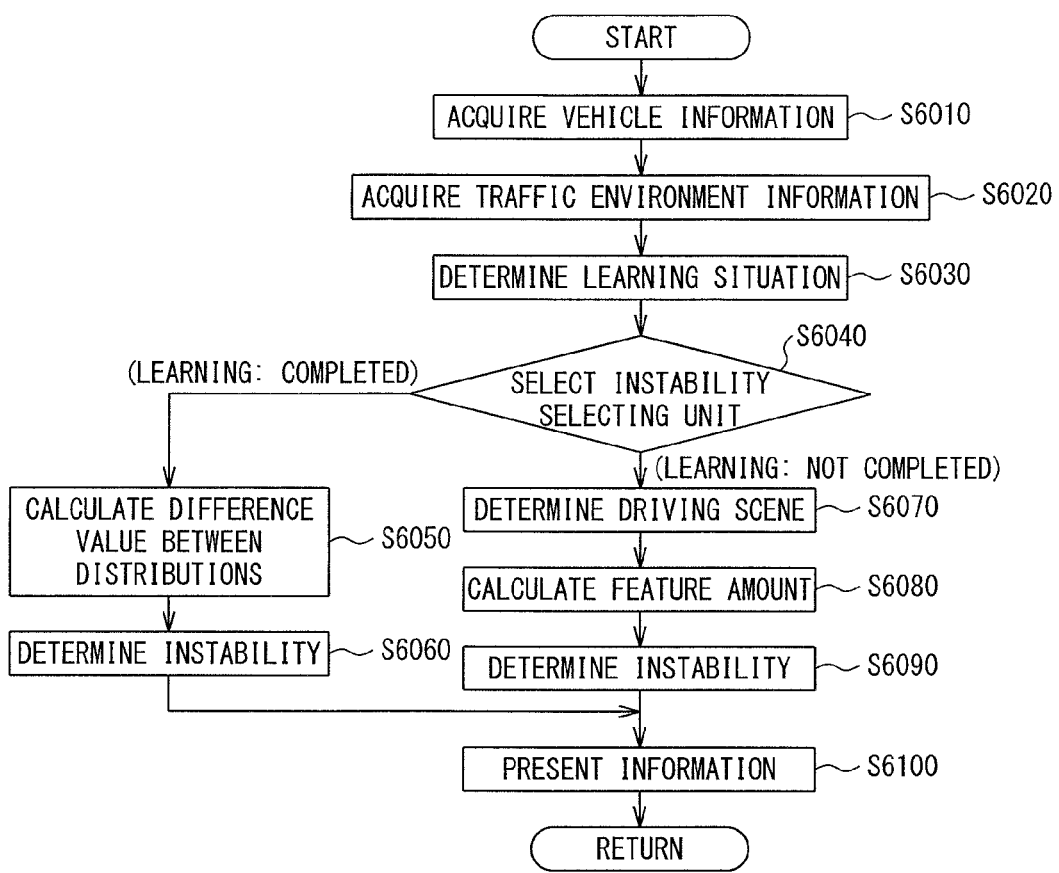
FIG. 16 is a diagram illustrating a process in an information providing unit according to the sixth embodiment of the present invention.

The process of the information providing unit 100A according to this embodiment will be described below with reference to the flowchart shown in FIG. 16.

In step S6010, the following data is acquired as vehicle information data which is information on the driving operation of a driver and a vehicle state due to the driving operation.

A steering angle, an accelerator pedal opening degree, a brake pedal operation amount, and a blinker indicating signal are acquired as the information on the driving operation of a driver. The blinker indicating signal is used as information for detecting a driving scene.

A vehicle velocity, a longitudinal G, and a transverse G are detected as the vehicle state information.

In step S6030, the information providing unit 100A acquires the intersection information as the traffic environment information through the navigation system 7.

In step S6030, the information providing unit 100A determines a learning situation through the same process as step S1030.

In step S6040, the information providing unit 100A determines whether the learning situation is a learning-completed situation on the basis of the degree of learning SD through the same process as in step S1040. When the learning situation is determined to be a learning-completed situation, the process progresses to step S6050. On the other hand, when the learning situation is determined to be a learning-uncompleted situation, the process progresses to step S6070.

In step S6050, the information providing unit 100A calculates the difference value between the distributions through the same process as step S1050. In step S6060, the unstable driving state is determined on the basis of the difference value through the same process as step S1060. Thereafter, the process progresses to step S6100.

On the other hand, in step S6070, the information providing unit 100A determines a driving scene (traffic environment). A right or left turning scene at an intersection, a preceding vehicle approaching scene, and the like can be considered as the driving scene, and the right or left turning scene at an intersection is exemplified.

It can be determined whether the driving scene is the right or left turning scene at an intersection, by using a method of determining an intersection on a navigation map or a process of determining an intersection on the basis of the blinker or the vehicle behavior.

In step S6080, the information providing unit 100A calculates the feature amount. A method same as the process in step S5100 of the fifth embodiment is used to calculate the feature amount in step S6080. That is, the feature amount is calculated by applying the magnitude of the transverse G instead of the braking operation to the process of step S5100.

In step S6090, the information providing unit 100A compares the feature amount calculated in step S6080 with a predetermined threshold value for determination and determines that the driving state is unstable when the feature amount is larger than the threshold value for determination.

The threshold value for determination is changed depending on the detected driving scene. For example, when the detected driving scene is a right or left turning scene at an intersection, the threshold value for determination is set to be lower than those of the other driving scenes.

In step S6100, similarly to step S1100, the information presenting process is performed when it is determined in step S6060 or S6090 that the driving state is unstable.

Here, the right or left turning scene at an intersection is exemplified as the driving scene, but a preceding vehicle approaching scene or the like may be used. In this case, in step S6070, it is determined whether the vehicle approaches a preceding vehicle. For example, when the distance to the preceding vehicle is equal to or less than a predetermined distance, it is determined that the driving scene is the preceding vehicle approaching scene. In step S6080, the same process as step S5100 is performed. In step S6090, the threshold value for determination is set to be lower than those of the other driving scenes when it is determined that the driving scene is the preceding vehicle approaching scene.

Here, steps S6010 and S6020 constitute the traveling state acquiring unit. Step S6050 constitutes the first traveling state distribution calculating unit and the first driving instability determining unit. Step S6030 constitutes the learning terminal determining unit. Steps S6070 to S6090 constitute the second driving instability determining unit. Step S6040 constitutes the instability selecting unit. Step S6100 constitutes the information presenting unit.

(Operational Advantages)

In this embodiment, the driving scene is determined, and then, a feature amount in a specific driving scene is calculated. The unstable state is determined on the basis of the feature amount in the specific driving scene (such as the right or left turning scene at an intersection or the decelerating scene relative to a preceding vehicle).

In this embodiment, the following advantages can be obtained in addition to the advantages of the first embodiment.

(1) The second driving instability determining unit includes a driving scene detecting unit that detects a specific driving scene and estimates a degree of instability by calculating a feature amount on the basis of the driving operation data of the specific driving scene detected by the driving scene detecting unit.

By specifying the driving scene, it is possible to easily grasp a small variation in driving operation appearing in the unstable state.

(2) The right or left turning scene at an intersection is detected as the specific driving scene, the feature amount is calculated from the driving characteristic at that time, and the degree of instability is estimated.

It is possible to accurately detect a state of a driver using the driving characteristics of the right or left turning scene at an intersection.

(3) The driving characteristics in the right or left turning scene employ the magnitude of the transverse G.

It is possible to accurately detect a behavior state at an intersection using the transverse G.

(4) The preceding vehicle approaching scene is detected as the specific driving scene, the feature amount is calculated from the driving characteristic of the deceleration operation at that time, and the degree of instability is estimated.

By detecting the decelerating operation characteristic of the preceding vehicle approaching scene, it is possible to accurately detect a state of a driver.

(5) The driving characteristics of the decelerating operation employ the magnitude of the TTC (time to collision) at the time of braking.

By using the time to collision, it is possible to accurately detect a state of a driver in the preceding vehicle approaching scene.

Priority is claimed on Japanese Patent Application No. 2011-94343 (filed on Apr. 20, 2011), the content of which is incorporated herein by reference in entirety.

While the present invention has been described with reference to the definite number of embodiments, the scope of the present invention is not limited thereto and improvements and modifications of the embodiments based on the above disclosure are obvious to those skilled in the art.

REFERENCE SIGNS LIST

SD: degree of learning
TTC: time to collision
1: accelerator pedal opening degree sensor
2: brake pedal operation amount sensor
3: steering angle sensor
4: vehicle velocity sensor
5: blinker detecting sensor
6: meter display
7: navigation system
8: G sensor
9: vehicle ahead detecting device
10: speaker
50: timer
100: controller
100A: information providing unit

The invention claimed is:

1. An information provision device for use in a vehicle, comprising:
    a processor configured to:
    acquire first traveling state data including at least one of a driving operation of a driver and a vehicle state;
    calculate a plurality of traveling state distributions including a traveling state distribution of an immediately-previous time range indicating a current traveling state and a traveling state distribution of a time range different from the immediately-previous time range on the basis of the first traveling state data;
    estimate first driving instability on the basis of a difference value between the calculated plurality of traveling state distributions;
    determine, as a result of a learning completion determination, that learning is completed when a predetermined learning time elapses from start of collection of the first traveling state data;
    detect whether a driving scene is a specific driving scene set in advance for use when the learning is not completed, when it is determined that the learning is not completed on the basis of a result of the learning completion determination;
    calculate, when it is determined that the learning is not completed on the basis of a result of the learning completion determination and the specific driving scene is detected, a feature amount of the traveling state distribution of the immediately-previous time range which indicates a current traveling state based on the first traveling state data in the detected specific driving scene and estimate second driving instability on the basis of the calculated feature amount;

select the first driving instability when the learning is completed and select the second driving instability when the learning is not completed, on the basis of a result of the learning completion determination; and present instability information based on instability selected between the first driving instability and the second driving instability to the driver.

2. The information provision device for use in the vehicle according to claim 1, wherein the processor is further configured to calculate a tendency of the feature amount on the basis of a history of the feature amount acquired at a constant interval and estimate the second driving instability on the basis of the calculated tendency.

3. The information provision device for use in the vehicle according to claim 1, wherein a right or left turn at an intersection is detected as the specific driving scene and the feature amount is calculated from a driving characteristic at that time.

4. The information provision device for use in the vehicle according to claim 3, wherein the magnitude of a transverse G is used as the driving characteristic of the right or left turn.

5. The information provision device for use in the vehicle according to claim 1, wherein a preceding vehicle approaching scene is detected as the specific driving scene and the feature amount is calculated from a driving characteristic of a decelerating operation at that time.

6. The information provision device for use in the vehicle according to claim 5, wherein the magnitude of a time to collision (TTC) at the time of braking is used as the driving characteristic of the decelerating operation.

7. The information provision device for use in the vehicle according to claim 1, wherein the processor is further configured to determine that the driving state is unstable when the calculated feature amount is greater than a predetermined threshold value for determination.

8. The information provision device for use in the vehicle according to claim 1, wherein the traveling state distribution is calculated based on an operation amount of steering operation.

9. The information provision device for use in the vehicle according to claim 8, wherein a steering entropy method is used in calculation based on the operation amount of steering operation.

10. The information provision device for use in the vehicle according to claim 1, wherein the processor is further configured to estimate the second driving instability using a time to collision (TTC).

11. The information provision device for use in the vehicle according to claim 1, wherein the processor is further configured to change the instability information to be presented depending on whether or not the learning is completed.

* * * * *